(12) United States Patent
Warden et al.

(10) Patent No.: US 8,327,843 B2
(45) Date of Patent: Dec. 11, 2012

(54) DRUG CONTAINMENT SYSTEMS WITH STICKS, RELATED KITS, DRY POWDER INHALERS AND METHODS

(75) Inventors: Jeffery Alan Warden, Raleigh, NC (US); Michael King, Durham, NC (US)

(73) Assignee: Oriel Therapeutics, Inc., Durham, NC (US)

( * ) Notice: Subject to any disclaimer, the term of this patent is extended or adjusted under 35 U.S.C. 154(b) by 1189 days.

(21) Appl. No.: 12/064,705

(22) PCT Filed: Aug. 23, 2006

(86) PCT No.: PCT/US2006/032925
§ 371 (c)(1),
(2), (4) Date: Jul. 9, 2008

(87) PCT Pub. No.: WO2007/024953
PCT Pub. Date: Mar. 1, 2007

(65) Prior Publication Data
US 2009/0165788 A1 Jul. 2, 2009

Related U.S. Application Data

(60) Provisional application No. 60/711,309, filed on Aug. 25, 2005.

(51) Int. Cl.
*B05D 7/14* (2006.01)
*A61M 15/00* (2006.01)
(52) U.S. Cl. ............................. 128/203.15; 128/203.12
(58) Field of Classification Search ............ 128/203.12, 128/203.14–203.15, 203.18–203.23, 203.26–203.28; 206/530–534.2, 538–539
See application file for complete search history.

(56) References Cited

U.S. PATENT DOCUMENTS

| | | | |
|---|---|---|---|
| 3,948,264 A | 4/1976 | Wilke et al. | 128/266 |
| 4,860,740 A * | 8/1989 | Kirk et al. | 128/203.15 |
| 5,533,502 A | 7/1996 | Piper | 128/203.21 |
| 5,655,523 A | 8/1997 | Hodson et al. | 128/315 |
| 5,727,607 A | 3/1998 | Ichikawa et al. | 141/67 |
| 5,909,829 A | 6/1999 | Wegman et al. | 222/232 |
| 5,947,169 A | 9/1999 | Wegman et al. | 141/71 |
| 6,029,663 A | 2/2000 | Eisele et al. | 128/203.21 |
| 6,055,980 A | 5/2000 | Mecikalski et al. | 128/203.15 |
| 6,089,227 A | 7/2000 | Nilsson | 128/203.5 |
| 6,123,068 A * | 9/2000 | Lloyd et al. | 128/200.24 |
| 6,132,416 A * | 10/2000 | Broselow | 604/506 |

(Continued)

FOREIGN PATENT DOCUMENTS
WO    WO 97/05918    2/1997
(Continued)

OTHER PUBLICATIONS

International Search Report and Written Opinion for International Application No. PCT/US06/32925; date of mailing Aug. 23, 2006.

(Continued)

*Primary Examiner* — Justine Yu
*Assistant Examiner* — Rachel Young
(74) *Attorney, Agent, or Firm* — Myers Bigel Sibley & Sajovec, P.A.

(57) ABSTRACT

Dry powder drug containment systems with a stick substrate and at least one dry powder receptacle or container that can be detached or opened to release dry powder in an inhaler. Related inhalers and kits of sticks are described.

19 Claims, 13 Drawing Sheets

U.S. PATENT DOCUMENTS

| | | | |
|---|---|---|---|
| 6,769,436 B2 | 8/2004 | Horian | 131/273 |
| 6,889,690 B2 | 5/2005 | Crowder et al. | 128/203 |
| 6,923,175 B2 | 8/2005 | Poole et al. | |
| 6,971,383 B2 | 12/2005 | Hickey et al. | 128/203.15 |
| 6,985,798 B2 | 1/2006 | Crowder et al. | 702/56 |
| 7,093,595 B2 * | 8/2006 | Nesbitt | 128/203.15 |
| 7,118,010 B2 | 10/2006 | Crowder et al. | 222/1 |
| 7,249,600 B2 * | 7/2007 | Chawla | 128/203.15 |
| 2001/0007853 A1 | 7/2001 | Dimarchi | |
| 2001/0053761 A1 | 12/2001 | Dimarchi | |
| 2003/0015191 A1 * | 1/2003 | Armstrong et al. | 128/200.21 |
| 2004/0025877 A1 | 2/2004 | Crowder | |
| 2004/0055598 A1 | 3/2004 | Crowder et al. | 128/203.15 |
| 2004/0055613 A1 | 3/2004 | Horian | 131/194 |
| 2004/0123864 A1 | 7/2004 | Hickey | |
| 2004/0206773 A1 * | 10/2004 | Ede et al. | 222/83 |
| 2005/0172961 A1 * | 8/2005 | Nesbitt | 128/203.15 |
| 2005/0263153 A1 * | 12/2005 | Young et al. | 128/203.15 |
| 2005/0274644 A1 * | 12/2005 | Williams-Hartman | 206/531 |
| 2008/0272022 A1 * | 11/2008 | Kulkarni et al. | 206/532 |

FOREIGN PATENT DOCUMENTS

WO      WO 00/64779      11/2000

OTHER PUBLICATIONS

Crowder et al., 2001: an Odyssey in Inhaler Formulation and Design, Pharmaceutical Technology, Jul. 2001, pp. 99-113.

Peart et al., New Developments in Dry Powder Inhaler Technology, American Pharmaceutical Review, 2001, pp. 37-45, vol. 4 n. 3.

Prime et al., Review of Dry Powder Inhalers, 26 Adv. Drug Delivery Rev., 1997, pp. 51-58.

Hickey et al., A new millennium for inhaler technology, Pharm. Tech., 1997, pp. 116-125, n. 6.

Wolff et al., Generation of Aerosolized Drugs, Aerosol. Med., 1994, pp. 89-106.

* cited by examiner

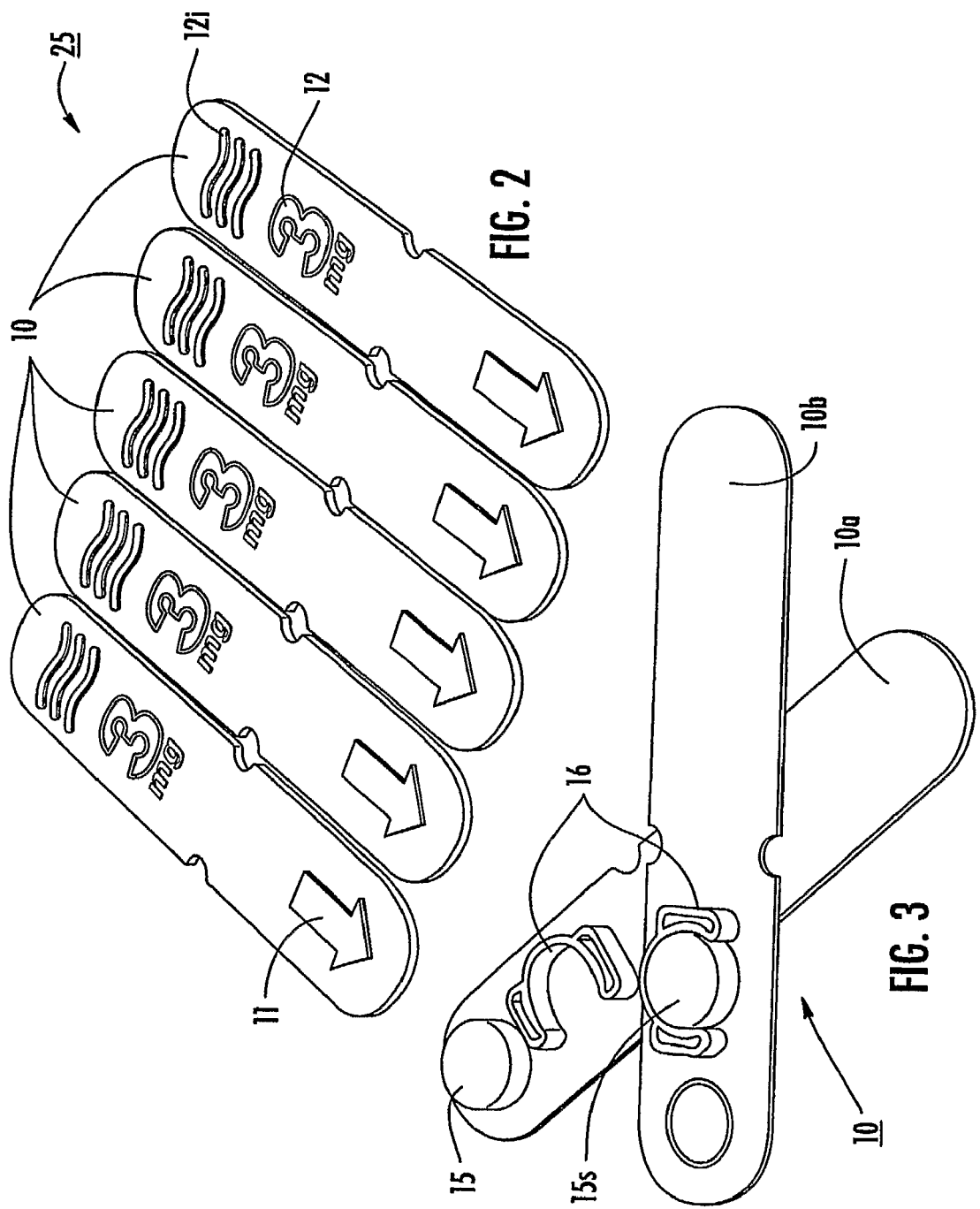

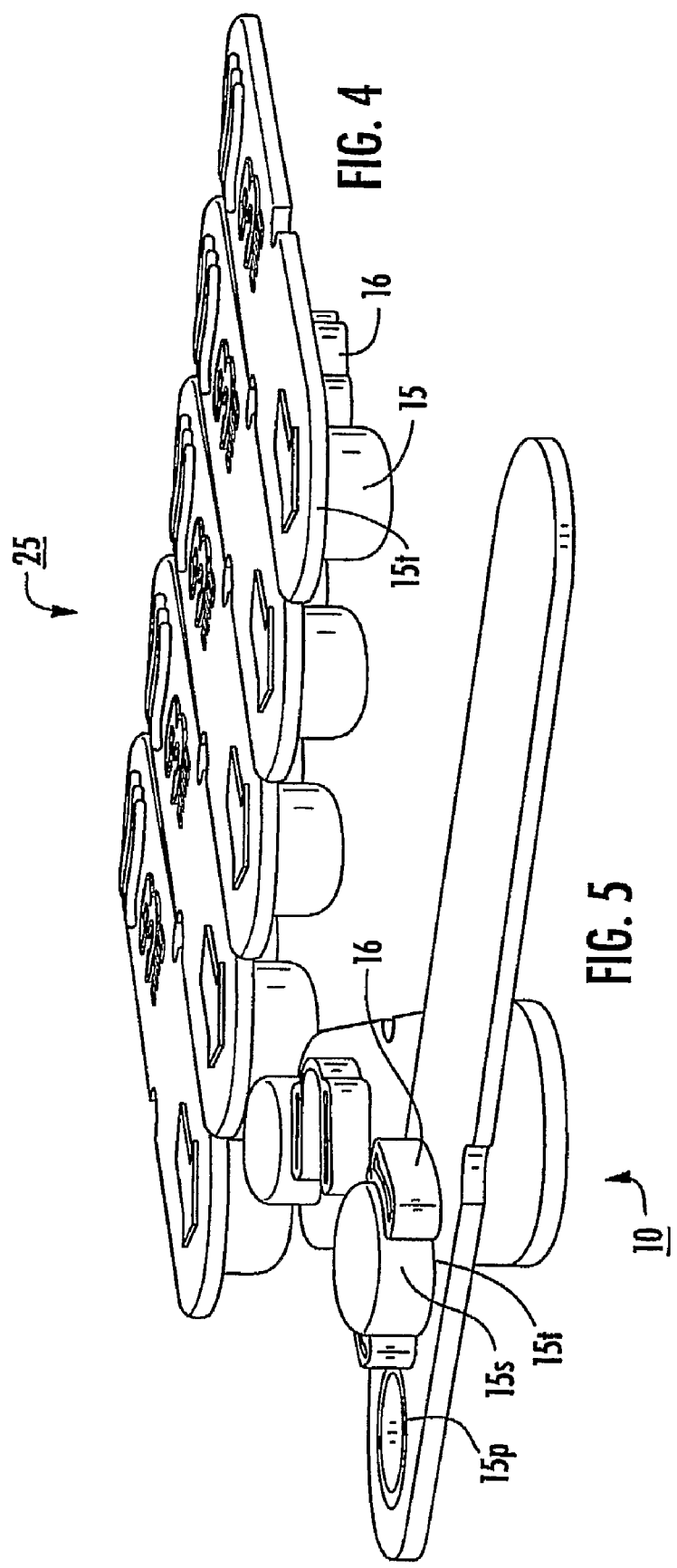

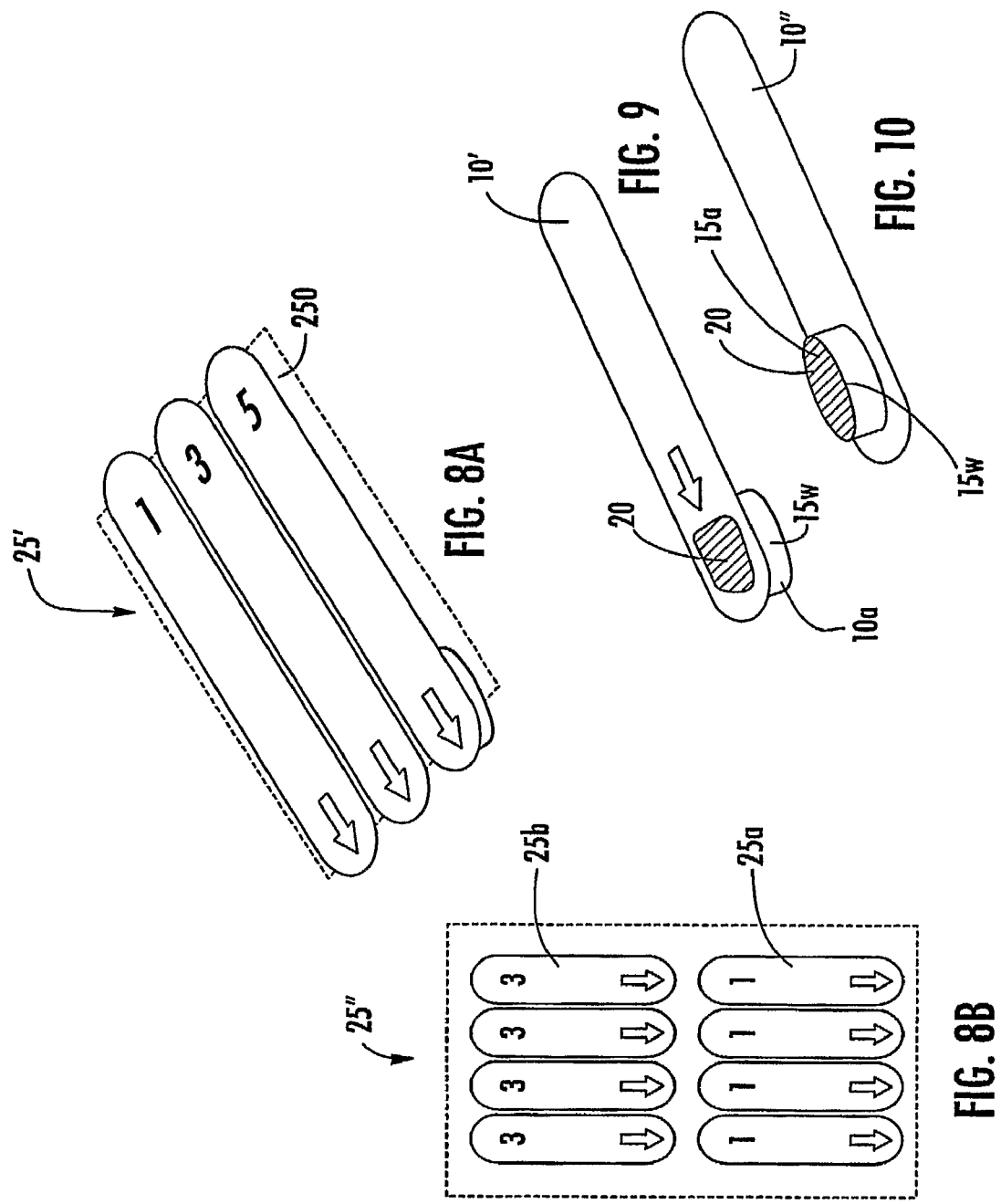

DRUG CONTAINMENT SYSTEMS WITH STICKS, RELATED KITS, DRY POWDER INHALERS AND METHODS

RELATED APPLICATIONS

This application is a 35 USC 371 national phase application of PCT/US2006/032925, filed Aug. 23, 2006, and claims the benefit of U.S. Provisional Patent Application Ser. No. 60/711,309, filed Aug. 25, 2005, the contents of which are hereby incorporated by reference as if recited in full herein.

FIELD OF THE INVENTION

The present invention relates to drug containment systems suitable for dry powders formulated for delivery as inhalant aerosols.

BACKGROUND OF THE INVENTION

Dry powder inhalers (DPIs) represent a promising alternative to pressurized pMDI (pressurized meted dose inhaler) devices for delivering drug aerosols without using CFC propellants. See generally, Crowder et al., 2001: *an Odyssey in Inhaler Formulation and Design*, Pharmaceutical Technology, pp. 99-113, July 2001; and Peart et al., *New Developments in Dry Powder Inhaler Technology*, American Pharmaceutical Review, Vol. 4, n. 3, pp. 37-45 (2001). Typically, the DPIs are configured to deliver a powdered drug or drug mixture that includes an excipient and/or other ingredients.

Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose. See generally Prime et al., *Review of Dry Powder Inhalers,* 26 Adv. Drug Delivery Rev., pp. 51-58 (1997); and Hickey et al., *A new millennium for inhaler technology,* 21 Pharm. Tech., n. 6, pp. 116-125 (1997).

In operation, DPI devices strive to administer a uniform aerosol dispersion amount in a desired physical form (such as a particulate size) of the dry powder into a patient's airway and direct it to a desired deposit site(s). If the patient is unable to provide sufficient respiratory effort, the extent of drug penetration, especially to the lower portion of the airway, may be impeded. This may result in premature deposit of the powder in the patient's mouth or throat.

A number of obstacles can undesirably impact the performance of the DPI. For example, the small size of the inhalable particles in the dry powder drug mixture can subject them to forces of agglomeration and/or cohesion (i.e., certain types of dry powders are susceptible to agglomeration, which is typically caused by particles of the drug adhering together), which can result in poor flow and non-uniform dispersion. In addition, as noted above, many dry powder formulations employ larger excipient particles to promote flow properties of the drug. However, separation of the drug from the excipient, as well as the presence of agglomeration, can require additional inspiratory effort, which, again, can impact the stable dispersion of the powder within the air stream of the patient. Unstable dispersions may inhibit the drug from reaching its preferred deposit/destination site and can prematurely deposit undue amounts of the drug elsewhere.

Further, some dry powder inhalers can retain a significant amount of the drug within the device, which can be especially problematic over time. In addition, the hygroscopic nature of many of these dry powder drugs may also require that the device be cleansed (and dried) at periodic intervals.

Some inhalation devices have attempted to resolve problems attendant with conventional passive inhalers. For example, U.S. Pat. No. 5,655,523 proposes a dry powder inhalation device which has a deagglomeration/aerosolization plunger rod or biased hammer and solenoid, and U.S. Pat. No. 3,948,264 proposes the use of a battery-powered solenoid buzzer to vibrate the capsule to effectuate the release of the powder contained therein. These devices propose to facilitate the release of the dry powder by the use of energy input independent of patient respiratory effort. U.S. Pat. No. 6,029,663 to Eisele et al. proposes a dry powder inhaler delivery system with a rotatable carrier disk having a blister shell sealed by a shear layer that uses an actuator that tears away the shear layer to release the powder drug contents. The device also proposes a hanging mouthpiece cover that is attached to a bottom portion of the inhaler. U.S. Pat. No. 5,533,502 to Piper proposes a powder inhaler using patient inspiratory efforts for generating a respirable aerosol and also includes a rotatable cartridge holding the depressed wells or blisters defining the medicament holding receptacles. A spring-loaded carriage compresses the blister against conduits with sharp edges that puncture the blister to release the medication that is then entrained in air drawn in from the air inlet conduit so that aerosolized medication is emitted from the aerosol outlet conduit. The contents of these patents are hereby incorporated by reference as if stated in full herein.

More recently, Hickey et al., in U.S. patent application Ser. No. 10/434,009 and PCT Patent Publication No. WO 01/68169A1 and related U.S. National Stage patent application Ser. No. 10/204,609, now issued U.S. Pat. No. 6,971,383, have proposed a DPI system to actively facilitate the dispersion and release of dry powder drug formulations during inhalation using powder specific signals which may promote or increase the quantity of fine particle fraction particles dispersed or emitted from the device over conventional DPI systems. The contents of these documents are hereby incorporated by reference as if recited in full herein.

Notwithstanding the above, there remains a need for alternative inhalers and/or drug containment systems that can be used with dry powders.

SUMMARY OF EMBODIMENTS OF THE INVENTION

In some embodiments, a drug containment system can employ a user-selectable stick that holds a unit dose of dry powder drug. Different sticks can hold different unit dose amounts that can be selected by a user (such as 1 mg, 3 mg, 5 mg and/or fractions thereof).

The sticks may be provided in frangible bundles with preferentially disposed perforations or an adhesive and the like that allows a user to detach or dislodge one from the others.

The drug containment systems (DCS) of the present invention may be particularly suitable for delivering inhalable insulin.

Methods of fabricating and/or filling drug containment systems can employ a stick, which may form part of the DCS and/or be used to facilitate handling by a user and/or to provide support during insertion into an inhaler for release of the drug from the DCS for delivery. The stick may also be configured to hold a detached member after it is separated from the stick to release the dry powder, thereby allowing a user to discard only one (combined item) rather than two items. The stick is typically single-use and disposable.

Some embodiments are directed to devices that include a stick with at least one drug containment system holding a bolus or sub-bolus amount of an inhalable drug.

In particular embodiments, the inhalable drug is a unitized dose amount of inhalable dry powder, such as insulin, which may be provided in a kit of sticks in at least three different unitized amounts.

Some embodiments are directed to pharmaceutical kits of inhalable medicaments. The kits can include a plurality of sticks holding each holding one or more respective unitized dose amounts of at least one inhalable drug.

In particular embodiments, the sticks include a plurality of sticks held together as at least one frangible bundle. The kit may include sticks with different unitized dose amounts of inhalable dry powder.

In some embodiments, the kit can include a plurality of bundles of sticks, with different bundles grouping different unitized dose amounts of the same inhalable dry powder.

Still other embodiments are directed to inhalers. The inhalers are configured to receive a stick holding a drug containment system, separate the drug containment system from the stick, release the drug held therein, then reposition the drug containment system on the stick at a different location.

In particular embodiments, the drug is an inhalable dry powder.

Additional embodiments are directed to methods of filling a drug containment system. The methods include: (a) providing a drug container; (b) filling the drug container with an inhalable drug; and (c) attaching the drug container to a stick.

Still other embodiments are directed to methods of operating a dry powder inhalers. The methods include: (a) inserting a stick holding a container with a unitized dose of dry powder into an inhaler; and (b) opening the container held by the stick to release dry powder into the inhaler.

The method may further include; detaching the opened container from the stick; then reattaching the detached container to the stick.

These and other objects and/or aspects of the present invention are explained in detail in the specification set forth below.

BRIEF DESCRIPTION OF THE FIGURES

FIG. 2 is a top perspective view of a kit of unit dose user-selectable drug containment systems according to embodiments of the present invention.

FIG. 3 is a bottom view of two unit dose drug containment systems illustrating one of them in an empty state and one ready for use according to embodiments of the present invention.

FIG. 4 is a side perspective view of the drug containment system kit shown in FIG. 2.

FIG. 5 is a side perspective view of the bottom of the two drug containment systems shown in FIG. 3.

FIG. 8A is a schematic illustration of a bundle of different unit dose sticks according to embodiments of the present invention.

FIG. 8B is a schematic illustration of two discrete bundles of unit dose sticks according to embodiments of the present invention.

FIG. 9 is a top perspective schematic illustration of an alternate configuration of a DCS according to embodiments of the present invention.

FIG. 10 is a bottom perspective schematic illustration of yet another alternative configuration of a DCS according to embodiments of the present invention.

DESCRIPTION OF EMBODIMENTS OF THE INVENTION

Figure 1:
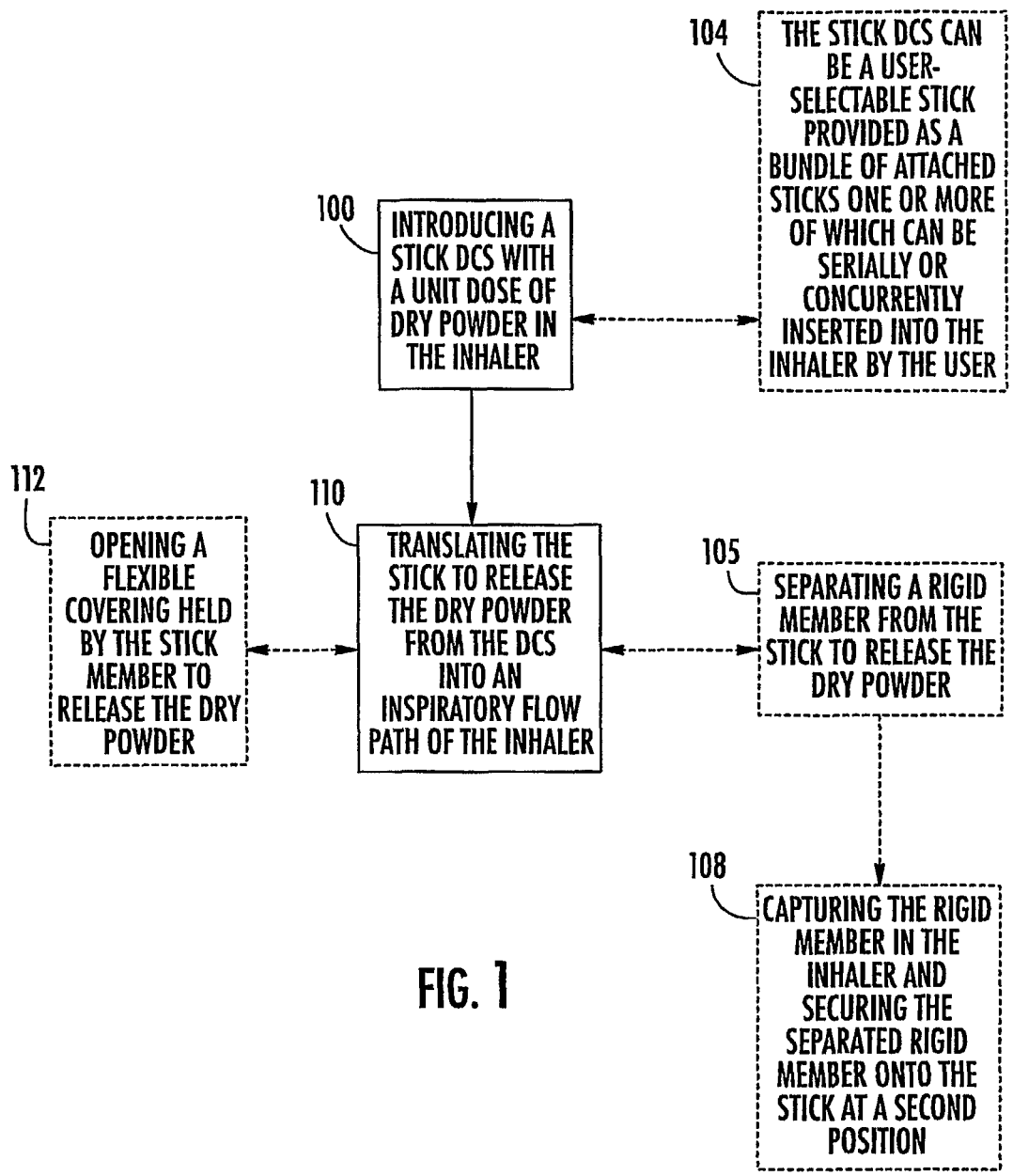
FIG. 1 is a flow chart of exemplary operations that can be used to operate an inhaler according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments. A feature described with respect to one embodiment can be used on a different embodiment.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this application and should not be interpreted in an idealized or overly formal sense unless expressly so defined herein.

In the description of the present invention that follows, certain terms are employed to refer to the positional relationship of certain structures relative to other structures. As used herein, the term "front" or "forward" and derivatives thereof refer to the general or primary direction that the dry powder travels as it is dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction.

The term "drug containment system" describes a disposable drug container device that holds at least one unitized, meted, bolus or sub-bolus amount of a target drug or medicament ("DCS"). The term "sealant layer" and/or "sealant material" includes configurations that have at least one layer or one material whether flexible or rigid; thus, such a phrase also includes multi-layer or multi-material sealant configurations.

The term "unitized" means a specified quantity of a pharmaceutical drug and/or medicament in terms of which the magnitudes of other quantities of the same or a different drug and/or medicament can be stated. The term "stick" refers to an elongate substrate support member that can hold or form at least a part of a DCS. The stick may be substantially planar, but may be formed in other shapes as well. The term "rigid member" (where used) means that the component is sufficiently rigid to be able to retain its shape, but may be able to flex side-to-side and/or up and down without collapsing on itself.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery.

The dry powder substance may include one or more active pharmaceutical constituents as well as biocompatible additives that form the desired formulation or blend. As used herein, the term "dry powder" is used interchangeably with "dry powder formulation" and means the dry powder can comprise one or a plurality of constituents or ingredients with one or a plurality of (average) particulate size ranges. The term "low-density" dry powder means dry powders having a density of about 0.8 g/cm$^3$ or less. In particular embodiments, the low-density powder may have a density of about 0.5 g/cm$^3$ or less. The dry powder may be a dry powder with cohesive or agglomeration tendencies.

In any event, individual dispensable quantities of dry powder formulations can be a single ingredient (such as pure drug) or a plurality of ingredients (a combination of drugs or a drug with an additive, such as an excipient(s)), whether active or inactive. The inactive ingredients can include additives added to enhance flowability or to facilitate aeorolization delivery to the desired target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, and composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroid, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or oligonucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). A conventional exemplary dry powder dose amount for an average adult is about 1-30 mg (but may be up to about 50 mg) and for an average adolescent pediatric subject is from about 1-10 mg. A typical dose concentration may be between about 1-2%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids. In certain embodiments, the administered bolus or dose can be formulated with an increase in concentration (an increased percentage of active constituents) over conventional blends.

Further, the dry powder formulations may be configured as a smaller administerable dose compared to the conventional 10-25 mg doses. For example, each administerable dry powder dose may be on the order of less than about 60-70% of that of conventional doses. In certain particular embodiments, using the active dispersal systems provided by certain embodiments of the DPI configurations of the instant invention, the adult dose may be reduced to under about 15 mg, such as between about 10 μg-10 mg, and more typically between about 50 μg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 μg.

In certain particular embodiments, during dose dispensing, the dry powder in a particular united DCS drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

Turning now to the figures, as shown in FIG. 1, a stick with a DCS can be insertably introduced and/or received in an inhaler (block 100). The stick and/or a detachable portion thereof can be translated to release the dry powder from the DCS into an inspiratory flow path of the inhaler (block 110). The stick can be a user-selectable stick provided as a bundle of detachably attached sticks and which may be individually (manually and/or serially) insertable into the user at a time of use (block 104). Optionally, two or more sticks may also be loaded into the inhaler concurrently for adjusting dose or administering combination drugs mixed in situ.

In some embodiments, the releasing can be carried out by separating a rigid member from the stick (block 105). The separation can be by cutting a lower portion of the rigid member from the underside of a primary surface of the stick. In particular embodiments, the rigid member can be captured by the inhaler after it is separated from the stick and may be (automatically) re-secured to the stick at a different location from where it was held prior to insertion into the inhaler (block 108).

In other embodiments, the dry powder can be released by opening a flexible covering held by (directly or indirectly on) the stick member (block 112). The flexible covering can comprise a foil, a polymer, and/or a laminate that can be punctured, burst, torn, punched or cut open.

Figure 17A:
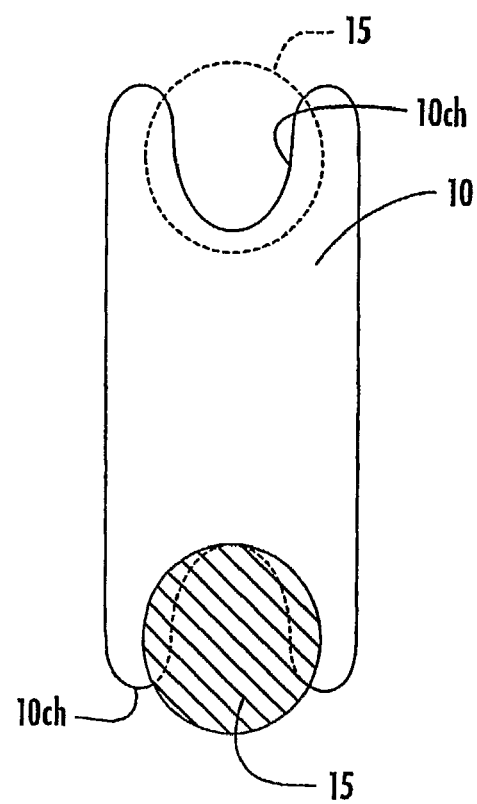
FIGS. 17A and 17B are top schematic views of alternate stick designs that hold at least one DCS according to embodiments of the present invention.
Figure 17B:
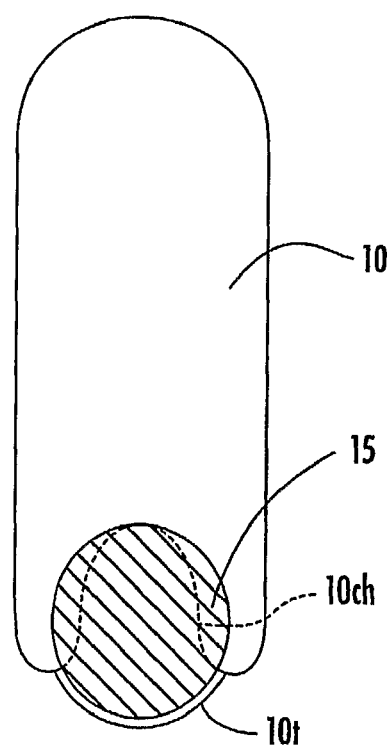

FIG. 2 illustrates a plurality of sticks 10 having at least one DCS 15. Each stick 10 can include a unitized dose amount of a dry powder. The top primary surface of the stick 10 can be a continuous closed surface. Alternatively, the surface may be discontinuous. For example, as shown in FIGS. 17A and 17B, the stick 10 can include a channel 10*ch* that holds the DCS 15. FIG. 17A also shows the empty after use or "used" container 15 may be held by a channel 10*ch* on the opposing end portion of the stick 10, while FIG. 17B illustrates the forward channel 10*ch* may hold by the full and empty DCS 15. FIG. 17B also illustrates a flexible tether 10*t* may be used to hold the DCS in the channel 10*ch*.

Referring again to FIG. 2, indicia 11 of use orientation (shown as an arrow) as to an insertion direction can be included. The stick 10 may also include indicia of dose amount 12 which can be visual and/or tactile indicia of unit dose amount. Other dose or use indicia may also be employed.

FIG. 2 illustrates that the sticks 10 can be bundled together as a kit of sticks 25 that can be individually detachable from the bundle or kit. The sticks 10 may be molded together with perforated or preferentially weaker seams, joints or releasing segments. In other embodiments, the sticks may be unitary members that are joined by tape, adhesive, welding or other attachment means or mounted together on a carrier member (250, FIG. 8A). The kit of sticks 25 may be provided as a planar row of sticks as shown, as a cartridge with a plurality of side-by-side or end-to-end layers, as stacked layers of single or multiple closely space and/or attached sticks (not shown) and the like, or combinations of same, in boxes, bags, bottles, or other containers, in any desired orientation or grouping. Other configurations or packages may be used. The kits of sticks 25 can be sterilized and/or held in sterilized packages for distribution or use, and which may be held in packages with releasable seals such as, for example, ZIPLOC configurations. The packages may be configured to provide moisture protection to the sticks 25 and/or DCS during storage and/or prior to use.

In some embodiments, the sticks 10 are single-use disposable. In other embodiments, the same stick 10 can be used to capture other DCS units held in a package. For example, one package may include a plurality of discrete DCS units that can be attached to a stick 10 by the user for subsequent insertion into an inhaler. As will be discussed further below, where different unitized dose amounts are used, the discrete units can be color coded to a stick 10. For example, a kit may include three sticks, each coded with visual indicia such as a particular color, such as blue, red and green. The discrete bodies can be color coded to match the corresponding stick for affirmation of dose amount. This color-coding or other visual indicia system may also be used during fabrication to facilitate proper filling at an OEM or drug filling site.

FIG. 3 illustrates the underside of two sticks 10, one in a ready-to-use configuration 10a and the other in a post-use configuration 10b. In this embodiment, the stick 10 includes a dry powder DCS container 15 that is detached to release the dry powder held therein into the inhaler (75, FIG. 6). The stick 10 may also include "a spent" container holder 16. The container 15 can be formed as a substantially rigid member that can be separated from the stick and may be reattached by slidably inserting the detached body into the holder 16. The holder 16 can frictionally engage and hold the body of the separated member 15s. The holder 16 can be a compartment with arms that flex to receive and hold the member 15s as shown. Other holder configurations may be used, including, for example, but not limited to, adhesives, two-sided tape, and other mechanical attachment brackets or retention mechanisms.

As shown in FIGS. 3 and 5, upon detachment, an upper portion 15p of the container 15 may remain on the stick 10 after the container is detached from the stick in the inhaler. In other embodiments, the entire container 15 can be removed (not shown) leaving substantially no remnants of the body itself (albeit traces of material may remain), and in yet other embodiments, a greater portion of the container can be left on the stick (also not shown).

Figure 16A:
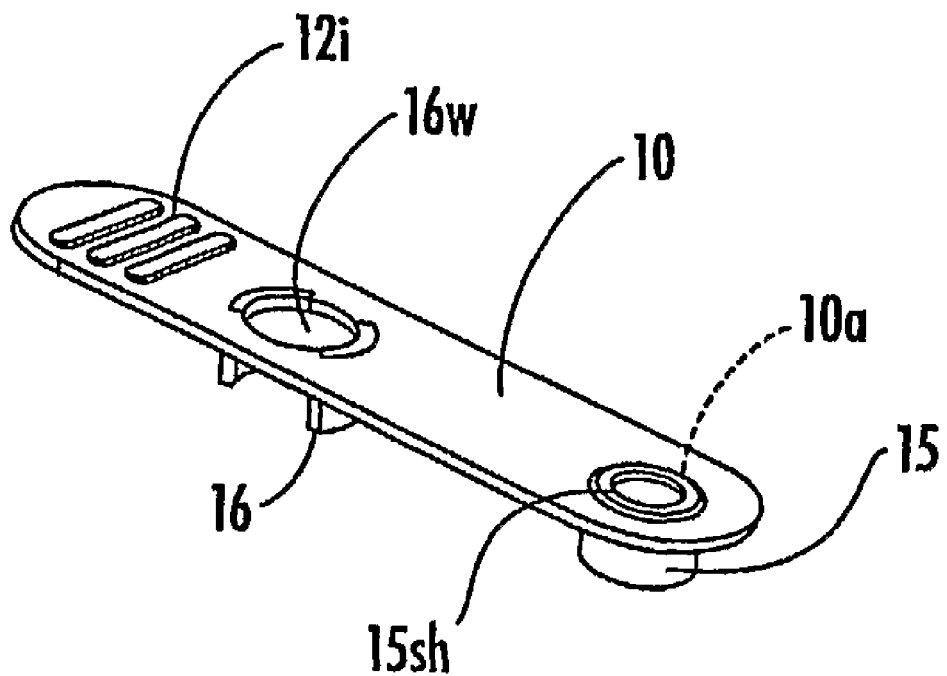
FIG. 16A is an enlarged side perspective view of an alternate stick configuration according to some embodiments of the present invention.

Referring to FIGS. 4 and 5, in some embodiments the container 15 has a cylindrical cup or bowl-like primary body 15p with an open top for dose filling. The stick 10 can overlie and close or reside over the top of the container 15t. Alternatively, as shown in FIG. 16A, the stick 10 may have a window 16w over the empty container holder 16 and/or an aperture 10a and the top of the container 15 can include a shoulder 15sh that extends over the aperture 10a.

In some embodiments, a sealant 20, which may be a relatively thin flexible sealant, such as foil or a polymer backed foil, can be placed over the dry powder in the container 15 to seal the container with the dry powder therein (not shown). In other embodiments, the stick 10 can be configured to seal the container 15 or the top of the container 15t can seal without an intermediate sealant. All substrates contacting the drug can be sterilized material and suitable for non-reactive contact therewith or include a coating to provide a non-reactive surface which inhibits oxygen permeability for a suitable shelf life.

The container 15 can be a discrete body that is heat-staked, ultrasonically or laser welded, adhesively attached, molded, or otherwise mounted to the stick 10. Typically, the container 15 will be mounted to an underside of the stick body. However, in other embodiments, the container 15 may be mounted to a top surface or in a channel or holder on the stick 10. In yet other embodiments, the stick can be molded with a sufficient depth to define a well 15w that forms at least a portion of the container 15 (FIGS. 9, 10).

Figure 6:
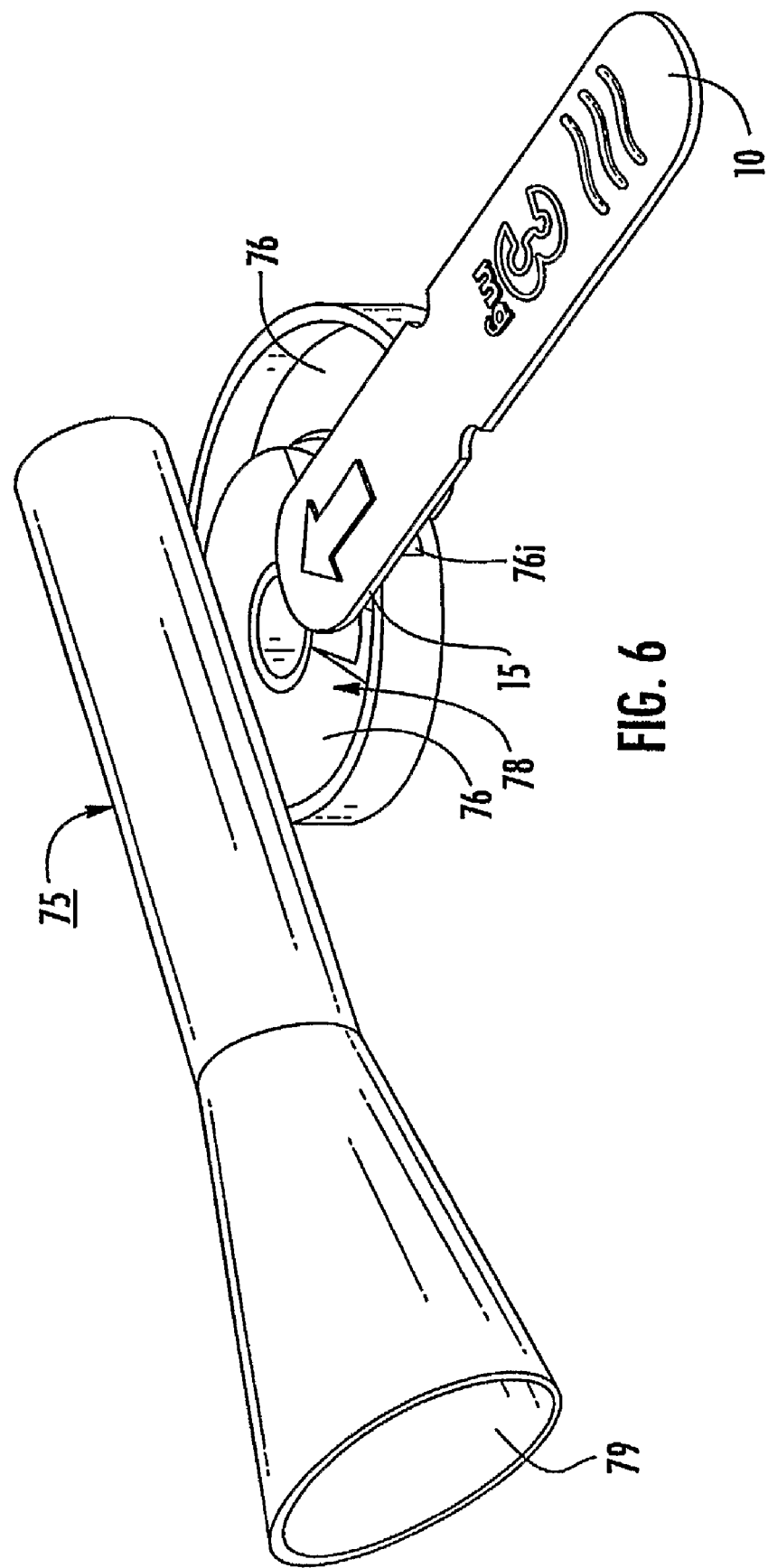
FIG. 6 is a perspective view of one of the unit dose containment systems shown in FIG. 2 positioned in an inhaler according to embodiments of the present invention.

As shown in FIG. 6, the stick 10 can be slidably inserted into an inhaler 75. In so doing, the container 15 can be directed into a channel 76. In some embodiments (those using a detachable or separatable container), the container 15 can be configured to be pushed, pulled, cut, or otherwise separated from the stick 10 in the inhaler 75. The separated portion of the container 15s can be captured in the inhaler channel 76 or otherwise captured (manually or automatically) for disposal.

Figure 7:
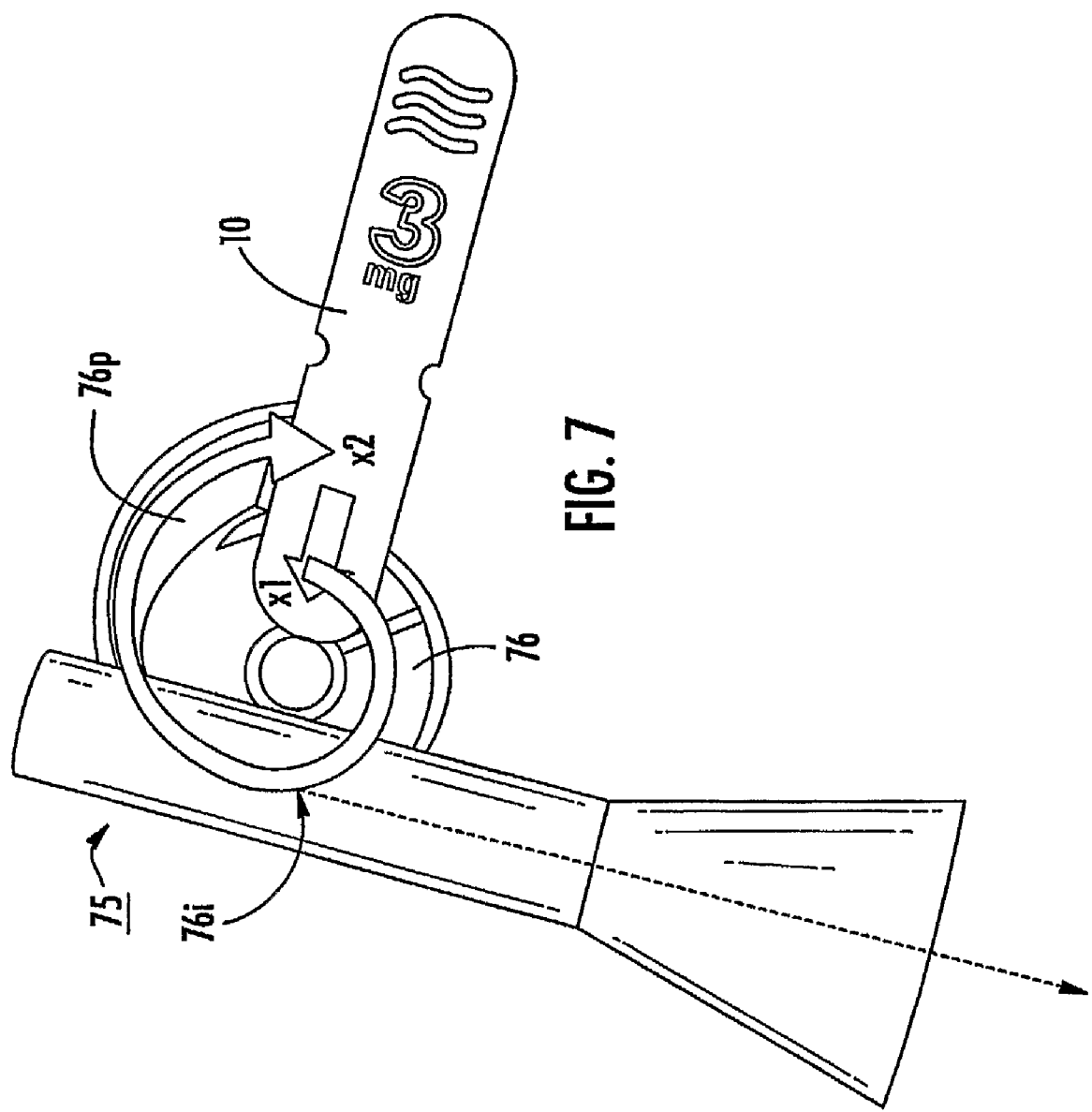
FIG. 7 is a top view of the inhaler and drug containment system shown in FIG. 6 illustrating an exemplary opening operation according to embodiments of the present invention.

As shown in FIG. 7, in some embodiments, the separated or opened container 15 travels in a channel 76 that defines a spiral travel path 76p. The stick may be stationary while the separated portion of the container 15s travels the defined travel path 76p. In some embodiments, the stick 10 may be configured to rotate (at least part of the path) with respect to the inhaler 75. The travel path direction is shown to be clockwise, but the reverse can also be used. A movement system such as a moving cartridge, belt, wheel(s), gear(s), rollers, moving floor, wall or ceiling, or a pushing or grasping pin or other mechanical configuration and/or air can be used to move the detached container through the travel path 76p. The stick 10 can remain inserted and locked into the channel 76 until the movement system or user pushes or otherwise moves the container 15 in a clockwise manner in the inhaler 75, while substantially aligned with a first release location on the stick, "$x_1$", to an inspiratory location or dry powder release port marked as "X" in FIG. 7, then to an exit location from the inhaler to a second location on the stick, "$x_2$", while in the inhaler, to reside a distance back on the stick 10 into the holder 16.

In some embodiments, as shown in FIG. 6 as the stick 10 approaches or enters the inhaler inlet 76i, the underside of the stick with the container 15 is forced forward to contact a cutting member or blade 78, which slices through an upper portion of the container 15 and detaches the container 15 to expose the dry powder for inhalation in the inspiratory airflow path 79.

In other embodiments, the container 15 is pushed or pulled off the stick 10 by contact with a pushing or pulling member (or pushing or pulling force) in communication with the channel 76. In yet other embodiments, an exposed sealant layer is opened (burst, cut, punctured, etc.) to open the DCS and expose the dry powder and a separate container member need not be detached (not shown, but see, e.g., FIGS. 9, 10).

In some embodiments, the detached container 15 is directed to travel through the remainder of the channel 76 during which it is pushed into the holder 16 and reattached to the stick 10. The used container 15d and stick 10 can be removed from the inhaler 75 and thrown away as a single device (instead of two separate disposal items). In other embodiments, the used container 15d can be captured in the inhaler 75 in a "trash bin" that is sealed off from the inspiratory path and can be periodically emptied by a user or captured for disposal with the inhaler (not shown).

The inhaler 75 can also include a display and a user input (not shown). The user input may include a "+" and a "−" input key. The user input can comprise contact pads, a touch screen or other input means, including a numeric entry device which can be used to track the amount of unitized bolus amounts of a target bolus amount of a drug needed by a user as will be discussed further below.

FIG. 5A illustrates that a bundle of sticks 25' can be provided in different unitized dose amounts. FIG. 8b illustrates that a kit of sticks 25 can include several attached packages 25a, 25b (1 mg, 3 mg, 5 mg or other denomination and/or fractions thereof, may also or alternatively be provided) of the same unitized dose amounts.

The sticks 10, 10', 10'' and/or wells 15w or containers 15 may be color coded, labeled, patterned or otherwise provided with different visual and/or tactile patterns or colors, to a respective unitized amount to facilitate proper assembly and/or use.

In some embodiments, unlike conventional inhalers, the inhaler 75 can be configured to allow a user to electronically input a variable target unitized bolus amount. Thus, particularly where a user will need to dispense medication from more than one vial or delivery system 10, the display can be configured to help a user determine/remember what has been dispensed and/or what remains to be dispensed to meet the target bolus amount.

Such practices differ from conventional drug delivery, in which a user typically takes the same bolus based on a dispensed prescription irrespective of the physiological condition of the user at a particular time (i.e., one or two capsules or pills) or 1-2 "puffs". Instead, a user may have disease that would benefit from administration of a contemporaneously adjustable unitized dose based on the condition of the user at that time. The inhaler 75 can allow the user to increment (via the "+" key") and/or decrement (via the "−" key) the display to identify in situ a target bolus number to the bolus amount then-needed. For example, a diabetic can take a blood or other body measurement that can be used to determine a target unitized bolus amount of medicament needed proximate in time to the measurement. The body measurement devices may be incorporated into the inhaler (not shown).

The drug(s) can be packaged in different unitized amounts in different drug containment systems 10, all of which can be dispensed from the inhaler 75. The different unitized amounts may be provided in a plurality of different unitized amounts, typically between 1-10. In some embodiments, the unitized amounts can be provided in kits as at least three different user selectable amounts, such as "1, "3" and "41" or "1", "3" and "5" or fractions thereof, such as 3.2, 3.3, etc. . . . The different unitized amounts may be identified by external indicia, such as drug containment system labeling, color, and or tube size. For example, each different unit size system can have a different color (such as blue, yellow, green, and the like). In particular embodiments, the inhaler 75 can dynamically display a color corresponding to a (currently) desired dose to provide feedback to allow the user to select the correct stick 10 for dispensing. That is, for a unitized dose of "3" which is held in a blue stick 10, the display can display a blue light or a blue icon that helps a user select the proper stick 10. The drug containments systems 10 can include electronically and/or optically readable data that identifies one or more of the unitized amount associated therewith and the type of medicament therein.

FIG. 9 illustrates another embodiment of a stick 10' that has an integral well 15w thereon. The well can be formed by a molded deeper segment on one end of the stick 10'. The stick 10' can have an aperture 10a that can be used for dose filling. A sealant 20 can be disposed over the top surface of the stick 10' and well 15w to seal the dry powder therein.

FIG. 10 illustrates yet another embodiment of a stick 10'' that includes an integral well with the stick defining a closed surface and the bottom of the well having a filling aperture 15a. The sealant 20 can be disposed over the bottom of the well to seal the dry powder for use.

Alternatively, the stick 10, 10', 10'' can be formed with a through cavity having open top and bottom portions, each of which may be sealed by a sealant layer 20 (not shown).

Figure 18:
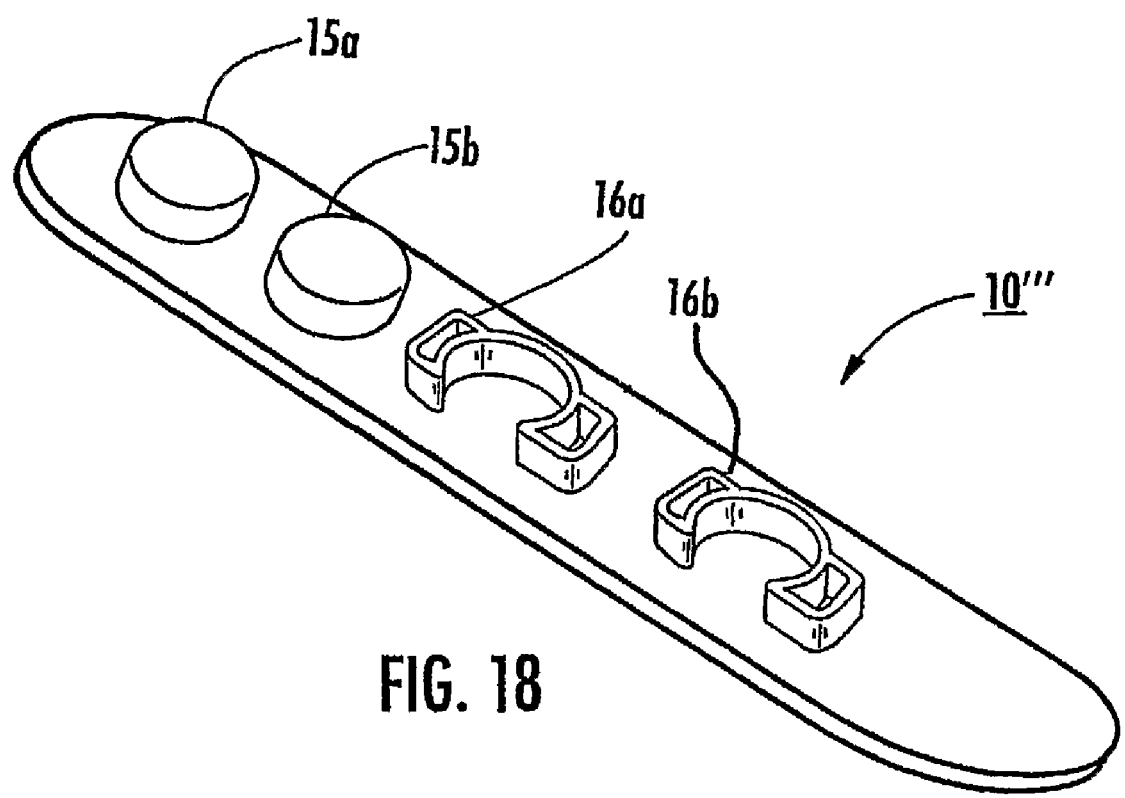
FIG. 18 is a schematic illustration of a multiple DCS container stick according to embodiments of the present invention.

It is also noted that a single container 15 or well 15w is shown on the sticks 10, 10', 10''. However, two or more co-joined or discrete containers or wells or combinations thereof may be held on a single stick 10 or several sticks can be used, either for adjustable dose amounts or for combination delivery of drugs. FIG. 18 illustrates a multi-container stick 10''', shown as two containers 15a, 15b. More containers may be held on one or more of the sticks in a bundle or kit, i.e., a kit can include sticks with single and multi-DCS containers. Multi-unit sticks 10''' can position the containers 15a, 15b substantially side-by-side or axially spaced apart. The respective containers 15a, 15b may include different powders that can be released in an inhaler at substantially the same time for combination therapies. The stick 10''' can include holders 16a, 16b for the respective "spent" DCS container. Further, although not shown, the containers 15a, 15b may be held on opposing primary surfaces of the stick. In addition, or alternatively, the containers 15a, 15b may be held on each opposing end portions or in a medial portion.

It is noted that the stick 10, 10', 10'', 10''' may be used in either configuration, e.g., with the DCS(s) 15 on top or on the bottom, typically depending on the inhaler interface. Further, the holder(s) 16 may be formed on the opposite surface as the DCS 15. If the orientation shown, for example, in FIG. 18, is considered the top, then indicia of dose/content may be included on the top surface with the DCS 15.

Figure 11:
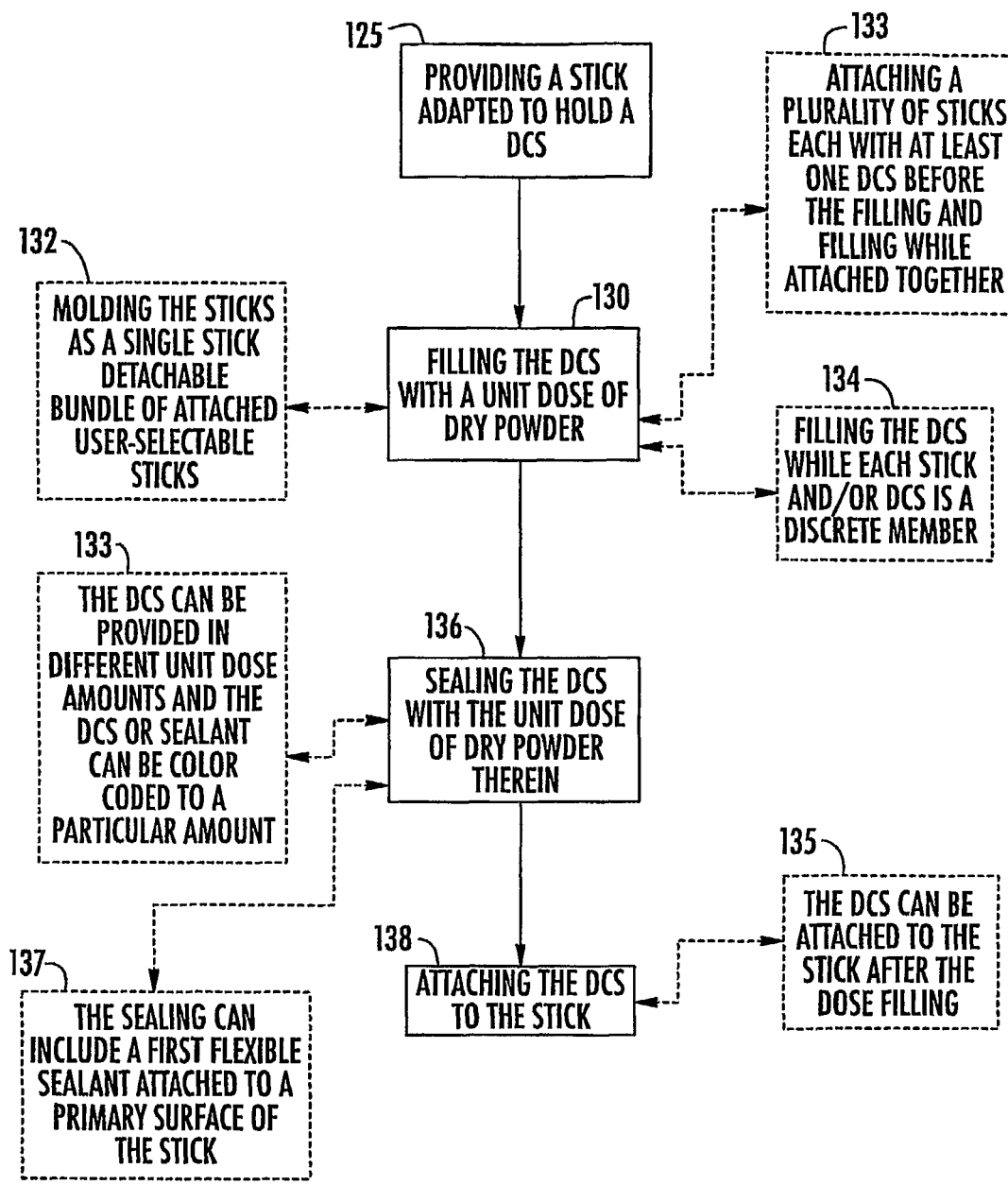
FIG. 11 is a flow chart of operations that can be used to fabricate/fill a DCS according to embodiments of the present invention.
Figure 12:
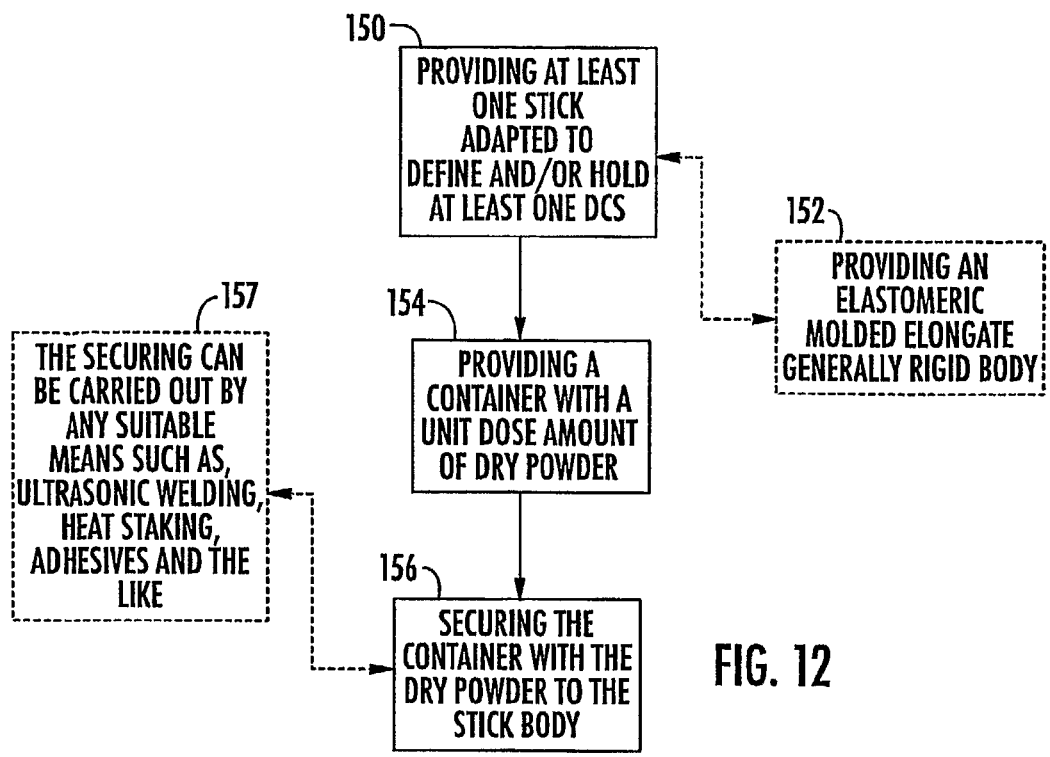
FIG. 12 is a flow chart of operations that can be used to fabricate/fill a DCS according to embodiments of the present invention.
Figure 13:
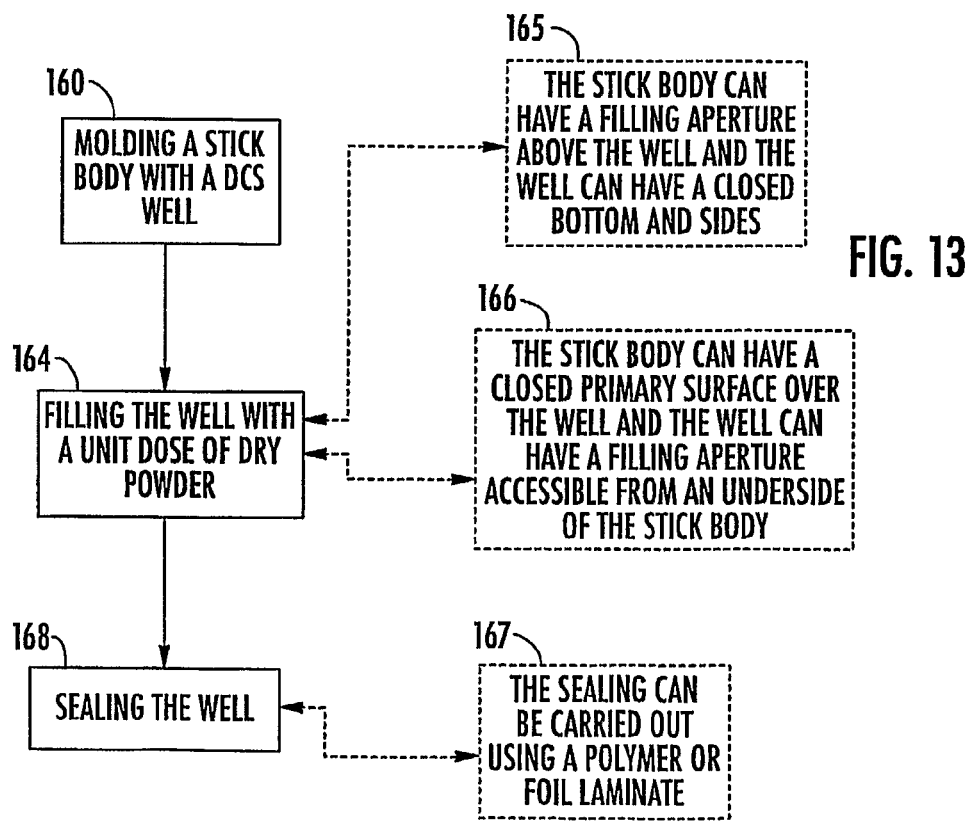
FIG. 13 is a flow chart of operations that can be used to fabricate/fill a DCS according to embodiments of the present invention.

FIGS. 11-13 illustrate exemplary operations that can be used to fabricate and/or fill one or more of the DCS devices described and/or shown herein. As shown in FIG. 11, a stick can be adapted to hold a DCS (block 125), the DCS can be filed with a unit dose of dry powder (block 130), the DCS can be sealed with the unit dose of dry powder therein (block 136). The DCS can be attached to the stick (block 138).

A plurality of the sticks may be attached before the filling and the filling can be carried out with them attached to each other (block 133). The filling can be done while each stick and/or container is separate (block 134). The DCS can be attached to the stick after dose filling (block 135) or before.

The sticks can be molded as an integral bundle of individually detachable sticks (block 132). The DCS can be provided in different dose amounts and the DCS body, stick and/or sealant can be color coded to a particular amount (block 133). The sealing can include a flexible sealant attached to a primary surface of the stick (block 137).

FIG. 12 illustrates exemplary operations or steps 150, 154 and 156 and optional steps 152 and 157. FIG. 13 illustrates exemplary steps 160, 164 and 168 and optional steps 165, 166 and 167.

The inhaler can include a circuit that controls certain operations of the inhaler. The circuit can include a power source and a controller that can automatically decrement the displayed number on the display after an active inhalation delivery. The controller may, in some embodiments, control the activation of a vibrator that is in communication with the inspiratory airflow path and/or drug containment system to promote release and/or fluidization of the dry powder during inhalation drug delivery.

The inhaler can also be configured to be able to electronically communicate with a remote location or device and/or provide additional data. The inhaler can be configured with a clock and can generate patient alarms, alerts and/or reminders to take the medicine or evaluate whether a medicine is desired at target intervals or (selectable) times. The inhaler can be configured to provide an "on" and/or "off" status indicator and/or generate one or more of: (a) a low battery charge warning; (b) a drug (over or under bolus) warning; and/or (c) a confirmation that the drug powder was successfully delivered (the above may be provide either via a visual and/or audible signal).

The inhaler can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler can be configured to communicate with a clinician or pharmacy for refills and/or patient compliance. The inhaler may also include a second peripheral device communication port (now shown).

In some embodiments, the controller can include computer program code and/or computer applications that communicate additional data to a user (optionally to the display) as noted above and/or communicate with another remote device (the term "remote" including communicating with devices that are local but typically not connected during normal inhalant use) device.

In some embodiments, the controller can be in communication with a signal generator for operating the vibrator. The controller can be programmed with or in communication with an electronic library of a plurality of desired dry powder excitation signals that can be automatically selected by the controller based on the data relayed and carried by the stick 10 corresponding to the drug type/drug disposed and/or amount therein. In this way, customized drug signals can be used to fluidize and provide repeatability disperse amounts of the dry powder within less than about 5% variation. Examples of suitable excitation signals are described in co-pending U.S. Patent Application Publication Nos. 2004-0025877-A1 and 2004-0123864, the contents of which are hereby incorporated by reference as if recited in full herein. For example, the excitation signals can be powder specific and employ a carrier frequency modulated by one or more (amplitude) modulating frequencies that can facilitate fluidic and reliable flow of the dry powder.

The vibrator can be any suitable vibrator configuration. The vibrator can be configured to vibrate the dry powder in the airflow path. In some embodiments, the vibrator can be configured to vibrate the drug compartment holding the dry powder. Examples of vibrators include, but are not limited to, one or more of: (a) ultrasound or other acoustic or sound-based sources (above, below or at audible wavelengths) that can be used to instantaneously apply non-linear pressure signals onto the dry powder; (b) electrical or mechanical deflection of the sidewalls and/or floor of the inhalation flow channel and/or drug compartment, which can include magnetically induced or caused vibrations and/or deflections (which can use electro or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electromechanical vibratory devices are described in U.S. Pat. Nos. 5,727,607, 5,909,829 and 5,947,169, the contents of which are incorporated by reference as if recited in full herein. In some particular embodiments, the vibrator includes at least one piezoelectric element, such as a piezoceramic component, and/or a piezoelectric polymer film. In some embodiments, the vibrator can comprise a signal generator held in the inhaler and a piezoelectric film held on the strip 10 or container 15.

The input signal may be customized to the particular powder being dispensed. See, e.g., U.S. Patent Application Publication No. US-2004-0025877-A1, the contents of which are hereby incorporated by reference as if recited in full herein. The input signal can be selected based on a programmed library of signals held in memory associated with the controller as noted above.

In certain embodiments, the inhaler can include visible indicia and/or can be configured to engage an inhaler to provide audible alerts to warn a user that the strip 10 is misaligned in the inhaler and/or that a dose was properly (and/or improperly) inhaled or released from the inhaler device. For example, certain dry powder dose sizes are formulated so that it can be difficult for a user to know whether they have inhaled the medicament (typically the dose is aerosolized and enters the body with little or no taste and/or tactile feel for confirmation). Thus, a sensor can be positioned in communication with the flow path in an inhaler and configured to be in communication with a digital signal processor or microcontroller each held in or on the inhaler. In operation, the sensor is configured to detect a selected parameter, such as a difference in weight, a density in the exiting aerosol formulation, and the like, to confirm that the dose was released.

Figure 14:
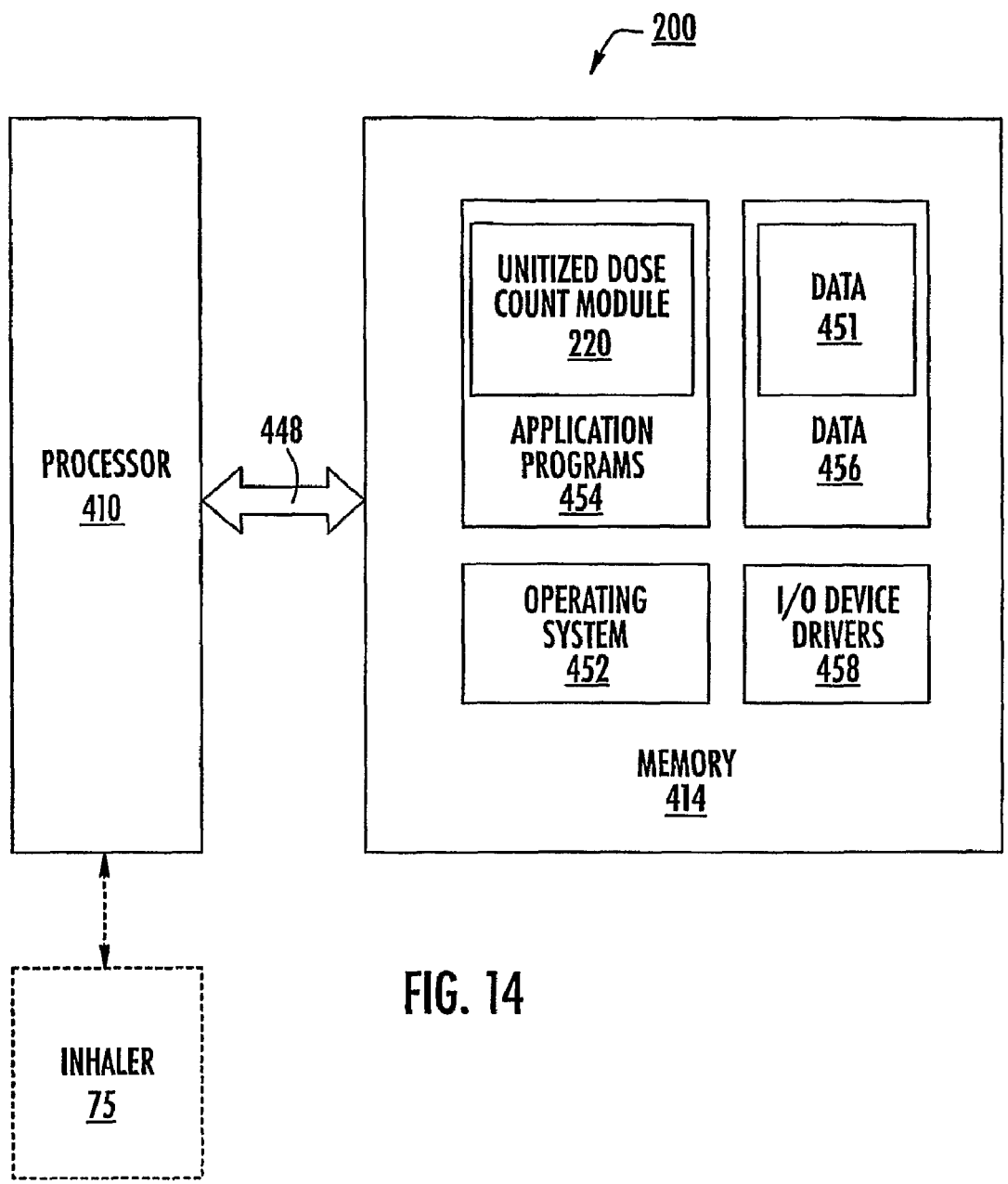
FIG. 14 is a schematic illustration of a data processing system for monitoring unitized dose amounts according to embodiments of the present invention.

FIG. 14 illustrates an example of a control system 200 that comprises a unitized dose count module 220. The control system 200 may be configured to communicate with a signal generator circuit in the inhaler 75. The control system can include a processor (such as a digital signal processor) 410 and electronic memory 414. The electronic memory can include, but is not limited to, cache, ROM, PROM, EPROM, EEPROM, flash memory, SRAM, and DRAM.

The system 200 may, in certain embodiments, also include a powder specific non-linear signal generator computer program module that provides the electrical signal characteristics for the drug being dispensed. The signal generator may include a library of a priori signals for different drugs, the appropriate one of which can be selected for operation by the inhaler depending on the drug(s) in the package. The module may be programmed into the memory 410. The system 200 may have a sleep or inactive (or off) mode that is turned to an active mode based on inhaler activation via input from a switch or a sensor. For example, the control system 200 may communicate with a power source such as a battery (typically a miniaturized battery, such as a digital camera or pancake type flat battery) to power the signal generator and transmit the electrical signal to the piezoelectric layer or other vibrator means. The activation may be carried out automatically based upon input from a sensor and/or activation from an "on" switch.

Examples of an amplitude-modified vibratory signal suitable for vibrating the inhaler holding the dry powder are described in co-pending U.S. patent application Ser. No. 10/434,009, the contents of which are incorporated by reference as if recited in full herein. The vibratory signal can include a kHz carrier frequency (such as about 5 kHz-50 kHz) modified by low modulating frequency (typically about 10-200 Hz). The frequency of the vibration can be modified to match or correspond to the flow characteristics of the dry powder substance held in the package to attempt to reach a resonant frequency(s) to promote uniform drug dispersion into the body. In some embodiments, a non-linear powder-specific dry powder vibratory energy signal comprises a plurality of selected frequencies that can be generated (corresponding to the particular dry powder(s) being currently dispensed) to output the particular signal corresponding to the dry powder(s) then being dispensed. As used herein, the term "non-linear" means that the vibratory action or signal applied to the package to deliver a dose of dry powder to a user has an irregular shape or cycle, typically employing multiple superimposed frequencies, and/or a vibratory frequency line shape that has varying amplitudes (peaks) and peak widths over typical standard intervals (per second, minute, etc.) over time. In contrast to conventional systems, the non-linear vibratory signal input can operate without a fixed single or steady state repeating amplitude at a fixed frequency or cycle. This non-linear vibratory input can be applied to the blister to generate a variable amplitude motion (in either a one, two and/or three-dimensional vibratory motion). The non-linear signal fluidizes the powder in such a way that a powder "flow resonance" is generated allowing active flowable dispensing.

In particular embodiments, the inhaler can include signal-generating circuitry and/or components held thereon or therein which, in operation, are in communication with the system to facilitate a complete release of particulate from the drug compartment. The signal generating circuitry may be programmed with a plurality of predetermined different input signals, or if the blister package dispenses only a single dry powder, the signal generator may be programmed with a single signal. Appropriate powder-specific signals, typically used for the channel vibration, can be determined experimentally and/or computationally at an OEM or evaluation site and input into the inhalers (via hardware and/or software components including programmable processors). For additional description of signals and operations to determine same, see co-pending and co-assigned U.S. patent application Ser. Nos. 10/434,009, 10/606,678, 10/607,389, and 10/606,676; the contents of these applications are hereby incorporated by reference in their entireties as if recited in full herein.

In some embodiments, a signal of combined frequencies can be generated to provide a non-linear signal to improve fluidic flow performance. Selected frequencies can be superimposed to generate a single superposition signal (that may also include weighted amplitudes for certain of the selected frequencies or adjustments of relative amplitudes according to the observed frequency distribution). Thus, the vibratory signal can be a derived non-linear oscillatory or vibratory energy signal used to dispense a particular dry powder. In certain embodiments, the output signal used to activate the piezoelectric blister channel may include a plurality of (typically at least three) superpositioned modulating frequencies and a selected carrier frequency. The modulating frequencies can be in the range noted herein (typically between about 10-500 Hz), and, in certain embodiments may include at least three, and typically about four, superpositioned modulating frequencies in the range of between about 10-100 Hz, and more typically, four superpositioned modulating frequencies in the range of between about 10-15 Hz.

While the present invention is illustrated, for example, with reference to the module 220 being an application program in FIG. 14, as will be appreciated by those of skill in the art, other configurations may also be utilized while still benefiting from the teachings of the present invention. Thus, the present invention should not be construed as limited to the configuration of FIG. 14, which is intended to encompass any configuration capable of carrying out the operations described herein.

The I/O data port can be used to transfer information between the data processing system 200 and the inhaler dispensing system controlled by the processor. These components may be conventional components such as those used in many conventional data processing systems which may be configured in accordance with the present invention to operate as described herein.

While the present invention is illustrated, for example, with reference to particular divisions of programs, functions and memories, the present invention should not be construed as limited to such logical divisions. Thus, the present invention should not be construed as limited to the configuration of FIG. 14 but is intended to encompass any configuration capable of carrying out the operations described herein.

Certain filling and/or inhaler use operations may be automated and/or carried out using computer programs and automated equipment.

Figure 15E:
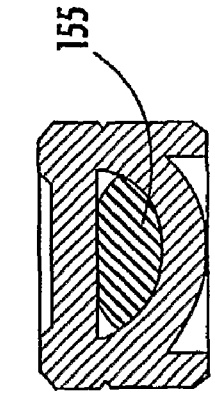
FIGS. 15B-15E are side section views of the device shown in FIG. 15A illustrating an exemplary fill and seal process.
Figure 15D:
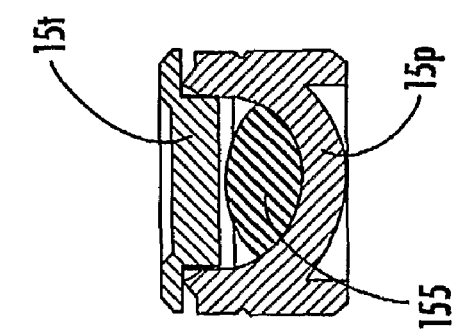
Figure 15C:
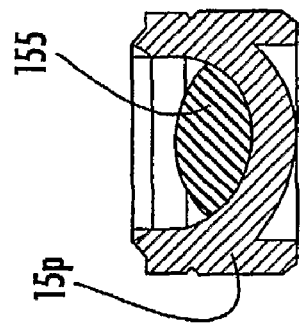
Figure 15A:
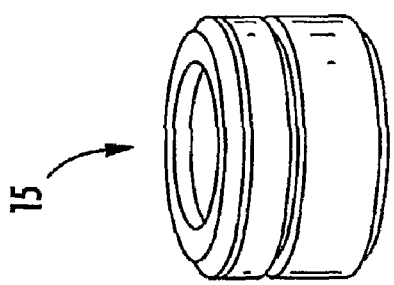
FIG. 15A is a perspective view of an exemplary unit-dose drug container according to some embodiments of the present invention.
Figure 15B:
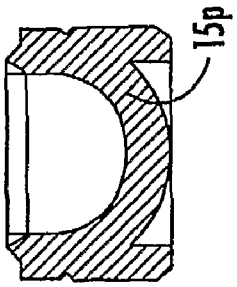

FIG. 15A illustrates an example of a DCS 15. While not wishing to be bound to a particular size, in some particular embodiments, the illustrated DCS 15 may be sized down from that scale shown, which can be between about a 3×-10× scale model. FIGS. 15B-15D illustrate an exemplary filling then sealing, process for dry powder 155.

Figure 16B:
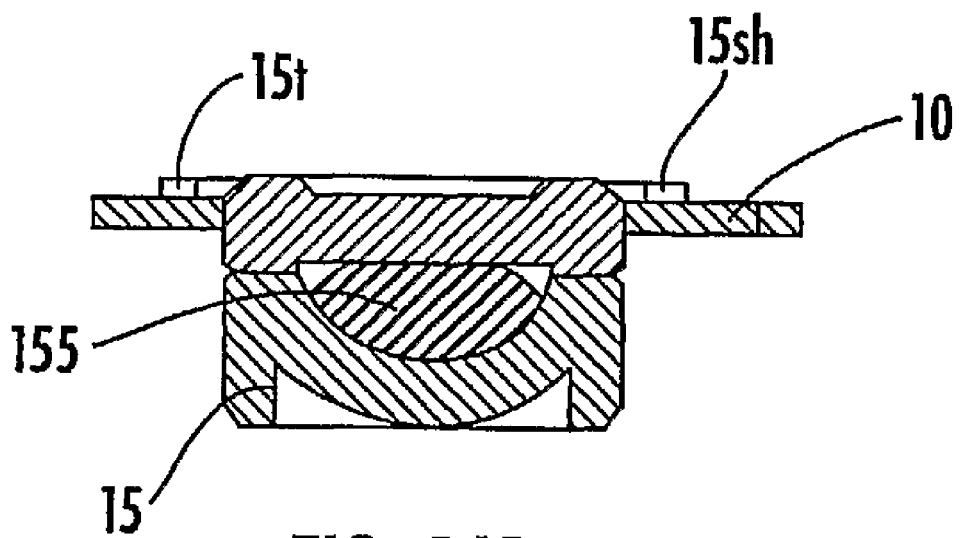
FIG. 16B is an end section view of the device shown in FIG. 16A illustrating the stick attached to the drug container with the drug therein according to some embodiments of the present invention.

FIG. 16A illustrates a stick 10 similar to that shown in FIG. 2, and FIG. 16B illustrates that the DCS 15 can be attached to the stick using a shoulder 15sh. The embodiment is enlarged between about 2-5×, and may be a 3× scale model of a suitable DCS 15 for some particular embodiments. The primary DCS body 15 can be filled and/or sealed before or after attachment to the stick 10. In particular embodiments, the DCS 15 can be attached, then filled and sealed, or filled and sealed, then attached. The stick 10 can be attached to the lid of the DCS 15 or may itself form the lid. Alternatively, the stick can be attached to another portion of the DCS 15 and a lid be formed by another member.

It is noted that although particularly suitable for dry powder inhalers or dry powder inhalant medicaments, the invention is not limited thereto and can be used to deliver or hold other medicines.

The flowcharts and block diagrams of certain of the figures herein illustrate the architecture, functionality, and operation of possible implementations of dry powder-specific dispensing and/or vibratory energy excitation means according to the present invention. In this regard, each block in the flow charts or block diagrams represents a module, segment, or portion of code, which comprises one or more executable instructions for implementing the specified logical function(s). It should also be noted that in some alternative implementations, the functions noted in the blocks may occur out of the order noted in the figures. For example, two blocks shown in succession may in fact be executed substantially concurrently or the blocks may sometimes be executed in the reverse order, depending upon the functionality involved.

In certain embodiments, the powder specific vibration energy signals are non-linear and the inhaler can include computer program code that automatically selectively adjusts the output of the vibration energy signal based on the identified dry powder being dispensed. The vibration energy output signals for the dry powders being dispensed can be based on data obtained from a fractal mass flow analysis or other suitable analysis of the dry powder being administered to the user. The inhaler may be particularly suited to dispense low-density dry powder.

Certain embodiments may be particularly suitable for dispensing medication to diabetic patients, cystic fibrosis patients and/or patients having diseases or impairments where variable bolus medicaments are desired. Other embodiments may be particularly suitable for dispensing narcotics, hormones and/or infertility treatments.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An inhaler and a device adapted to cooperate with an inhaler comprising an elongate substantially rigid stick with at least one drug containment system comprising a detachable cup-like body attached to a first end portion of the stick holding a bolus or sub-bolus amount of an inhalable drug, wherein the first end portion of the stick is configured to be releasably, slidably inserted into the inhaler by a user with an opposing second end portion extending outside the inhaler, and wherein the inhaler detaches the cup-like body from the stick to release the inhalable drug, and wherein the inhaler is configured to reattach a respective cup-like body to a respective stick at a post-use location that is different from a pre-use location.

2. A device according to claim 1, further comprising a unitized dose amount of inhalable dry powder residing in the cup-like body, wherein the stick is a planar stick having upper and lower primary surfaces, and wherein the cup-like body abuts the lower primary surface proximate the first end portion of the stick.

3. A device according to claim 1, wherein the stick is a planar stick having opposing first and second end portions, wherein the cup-like body is a substantially rigid disk shaped body held by the first end portion of the stick.

4. A device according to claim 2, further comprising visual and/or tactile indicia of unitized dose amount on the stick corresponding to the dry powder therein, wherein the cup-like body and stick have a defined color associated with a unitized dose amount of the drug in the cup-like body.

5. A device according to claim 2, wherein the dry powder comprises insulin.

6. A pharmaceutical kit of inhalable medicament, the kit comprising a plurality of the devices of claim 1, each stick holding one or more cup-like bodies with respective unitized dose amounts of at least one inhalable drug.

7. A kit according to claim 6, wherein a plurality of the sticks are held together as at least one frangible bundle.

8. A kit according to claim 7, wherein the at least one frangible bundle has preferentially disposed perforations residing between sticks.

9. A kit according to claim 7, wherein the frangible bundle comprises an adhesive that allows a user to detach or dislodge one stick from the others.

10. A kit according to claim 6, wherein the sticks are adhesively held together as a bundle on a flexible substrate.

11. A kit according to claim 6, wherein the kit comprises sticks with different unitized dose amounts of inhalable dry powder, and wherein sticks of different unitized amounts have defined different colors.

12. A kit according to claim 6, wherein the kit comprises a plurality of bundles of sticks, with different bundles grouping different unitized dose amounts of the same inhalable dry powder, and wherein sticks of different unitized amounts have defined different colors.

13. An inhaler with user inserted sticks, wherein the inhaler releasably receives the user-inserted, then withdrawn, substantially rigid sticks, each stick holding a substantially rigid cup-like body on a first end portion thereof, the cup-like body comprising a unit amount of dry powder drug, whereby, when inserted, the inhaler detaches the cup-like body from the respective stick and releases the drug held therein, wherein the inhaler is configured to reattach a respective cup-like body to a respective stick at a post-use location that is different from a pre-use location.

14. An inhaler according to claim 13, wherein the drug is an inhalable dry powder for treating diabetes.

15. A method of operating a dry powder inhaler, comprising:
inserting a first rigid substantially planar stick holding a cup-like body on a first end portion thereof with a unitized dose of dry powder into an inhaler; then
automatically detaching the cup-like body held by the stick to release dry powder into the inhaler; then
reattaching the cup-like body from the stick at a post-use location that is different from a pre-use location; and
removing the stick from the inhaler,
wherein the inserting, detaching, reattaching and removing steps are repeated to serially deliver respective unitized dose amounts of dry powder to a user.

16. An inhaler according to claim 13, further comprising a controller with a dose count module, wherein the sticks comprise electronically and/or optically readable dose indicia.

17. A kit according to claim 11, wherein different unitized dose amounts of the dry powder are held by defined different color sticks thereby allowing a user ease in identification of the unitized dose amounts.

18. A method according to claim 15, further comprising electronically and/or optically reading dose amount indicia on a respective stick to identify a unitized dose amount of the dry powder in the cup-like body, and displaying the amount to a user on a display held by the inhaler.

19. A device according to claim 1, wherein the stick includes an arrow on an upper surface thereof to thereby provide a user with visual indicia of proper insertion direction.

* * * * *

UNITED STATES PATENT AND TRADEMARK OFFICE
CERTIFICATE OF CORRECTION

PATENT NO. : 8,327,843 B2
APPLICATION NO. : 12/064705
DATED : December 11, 2012
INVENTOR(S) : Warden et al.

It is certified that error appears in the above-identified patent and that said Letters Patent is hereby corrected as shown below:

In the Specification

Column 11, Line 6: Please correct "FIG. 5A illustrates" to read -- FIG. 8A illustrates --.

Column 11, Lines 11-16: Please correct to read as one continuous paragraph.

Column 11, Line 46: Please replace "such as "1, "3" and "41" or" to read -- such as "1", "3" and "4" or --.

Column 13, Line 19: Please correct "(now shown)." to read -- (not shown). --.

Signed and Sealed this
Seventeenth Day of September, 2013

Teresa Stanek Rea
*Deputy Director of the UnitedStates Patent and Trademark Office*